United States Patent
Willis et al.

(10) Patent No.: US 9,205,171 B2
(45) Date of Patent: Dec. 8, 2015

(54) HYDROGEN OUT GAS OF POROUS METAL SCAFFOLD

(71) Applicant: Zimmer, Inc., Warsaw, IN (US)

(72) Inventors: Edward M. Willis, Hoboken, NJ (US); Mae Abiog, Edison, NJ (US); Joseph R. Vargas, Garnerville, NY (US)

(73) Assignee: Zimmer, Inc., Warsaw, IN (US)

( * ) Notice: Subject to any disclaimer, the term of this patent is extended or adjusted under 35 U.S.C. 154(b) by 220 days.

(21) Appl. No.: 13/926,353

(22) Filed: Jun. 25, 2013

(65) Prior Publication Data

US 2014/0027027 A1    Jan. 30, 2014

Related U.S. Application Data

(60) Provisional application No. 61/675,022, filed on Jul. 24, 2012.

(51) Int. Cl.
| | |
|---|---|
| *C21D 1/74* | (2006.01) |
| *C21D 1/773* | (2006.01) |
| *C23D 13/00* | (2006.01) |
| *C22F 1/02* | (2006.01) |
| *A61L 27/04* | (2006.01) |
| *A61L 27/56* | (2006.01) |

(52) U.S. Cl.
CPC ............ *A61L 27/04* (2013.01); *A61L 27/56* (2013.01); *C21D 1/74* (2013.01); *C21D 1/773* (2013.01); *C22F 1/02* (2013.01); *C23D 13/00* (2013.01)

(58) Field of Classification Search
CPC ............ C21D 1/74; C21D 1/773; C22F 1/02; C23D 13/00
See application file for complete search history.

(56) References Cited

U.S. PATENT DOCUMENTS

| | | | |
|---|---|---|---|
| 5,108,517 A | * | 4/1992 | Kimura et al. ............... 148/669 |
| 5,282,861 A | | 2/1994 | Kaplan |
| 5,303,904 A | * | 4/1994 | Kemp ........................ 266/252 |

* cited by examiner

*Primary Examiner* — George Wyszomierski
*Assistant Examiner* — Tima M McGuthry Banks
(74) *Attorney, Agent, or Firm* — Schwegman Lundberg & Woessner, P.A.

(57) ABSTRACT

Systems and methods for hydrogen out gas of a porous metal scaffold are disclosed. A method can comprise heating a porous metal scaffold for a period of time sufficient to remove at least a portion of a hydrogen concentration from the scaffold, subjecting the porous metal scaffold to a vacuum while heating it, flowing an inert gas through or around the porous metal scaffold while heating it, and enhancing a mechanical property of the porous metal scaffold. Heating of the porous metal scaffold can include maintaining a temperature of the scaffold between 1035° C. and 1065° C., inclusive. A system can comprise a reaction chamber, a heater, a gas feed, and a vacuum apparatus. The heater can be configured to heat the reaction chamber and the porous metal scaffold, while the gas feed and the vacuum apparatus respectively flow inert gas and subject the porous metal scaffold to a vacuum.

21 Claims, 5 Drawing Sheets

HYDROGEN OUT GAS OF POROUS METAL SCAFFOLD

CLAIM OF PRIORITY

This application claims the benefit of U.S. Provisional Patent Application Ser. No. 61/675,022, filed on Jul. 24, 2012, the benefit of priority of which is claimed hereby, and is incorporated by reference herein in its entirety.

BACKGROUND

Prosthetic devices can replace or augment body components or portions of body components that cannot be regenerated or are no longer functioning properly. Examples of prosthetic devices include heart valves, pacemakers, spinal implants, dental implants, breast implants, collagen for soft tissue augmentation, and orthopedic devices, such as artificial knee, hip, and ankle joints.

Some prosthetic implants can include a porous scaffold material. Porous scaffolds can be used to provide structural support to a patient's bone or other tissue. Porous scaffolds can also be used to provide an attachment structure for the patient's bone or other tissue to couple or attach to, such as via tissue in-growth or bonding between the tissue and the porous scaffold.

SUMMARY

This patent document discloses systems and methods for treating a porous metal scaffold to reduce effects of hydrogen embrittlement. The present inventors recognize, among other things, that when excessive hydrogen atoms are present within the structure of a porous metal scaffold, the hydrogen can cause impaired mechanical properties, including reduced ductility, mechanical strength, or stiffness or increased brittleness, also referred to herein as "hydrogen embrittlement." The present systems and methods can reverse or reduce these impaired mechanical properties by removing at least a portion of a hydrogen concentration from the porous metal scaffold, thereby restoring mechanical strength or stiffness to the porous metal scaffold.

A method can comprise heating a porous metal scaffold for a period of time sufficient to remove at least a portion of a hydrogen concentration from the scaffold, subjecting the porous metal scaffold to a vacuum while heating the scaffold, flowing an inert gas through or around the porous metal scaffold while heating the scaffold; and increasing a mechanical property of the porous metal scaffold. Heating of the porous metal scaffold can include maintaining a temperature of the scaffold between 1035° C. and 1065° C., inclusive.

A system can comprise a reaction chamber configured to receive a porous metal scaffold, a heater, a gas feed, and a vacuum apparatus. The heater can be configured to heat the reaction chamber and the porous metal scaffold to a temperature between 1035° C. and 1065° C., inclusive, for a period of time sufficient to remove at least a portion of a hydrogen concentration from the scaffold. The gas feed can be configured to flow an inert gas through or around the porous metal scaffold while the heater heats the reaction chamber and the scaffold. The vacuum apparatus can be configured to subject the porous metal scaffold to a vacuum while the heater heats the scaffold.

These and other examples and features of the present systems and methods will be set forth in part in the following Detailed Description. This Summary is intended to provide an overview of the present subject matter, it is not intended to provide an exclusive or exhaustive explanation. The Detailed Description below is included to provide further information about the present systems and methods.

BRIEF DESCRIPTION OF THE DRAWINGS

In the drawings, like numerals can be used to describe similar elements throughout the several views. Like numerals having different letter suffixes can be used to represent different views of similar elements. The drawings illustrate generally, by way of example, but not by way of limitation, various embodiments discussed in the present document.

DETAILED DESCRIPTION

Systems and methods for treating a porous metal scaffold to reduce effects of hydrogen embrittlement are disclosed. Treatment of the porous metal scaffold can remove at least a portion of a hydrogen concentration, thereby increasing a mechanical property of the porous metal scaffold, such as ductility or mechanical strength, which can be advantageous for orthopedic or other prosthetic implant uses. A method can include heating the porous metal scaffold for a period of time sufficient to remove at least a portion of a hydrogen concentration from the scaffold, subjecting the porous metal scaffold to a vacuum while heating the scaffold, flowing an inert gas through or around the porous metal scaffold while heating the scaffold, and enhancing a mechanical property of the porous metal scaffold An example of a porous metal scaffold for prosthetic implant uses, such as orthopedic bone restoration or joint repair, is described in U.S. Pat. No. 5,282,861 to Kaplan, entitled "Open Cell Tantalum Structures For Cancellous Bone Implants and Cell and Tissue Receptors," which is incorporated herein by reference.

Figure 1:
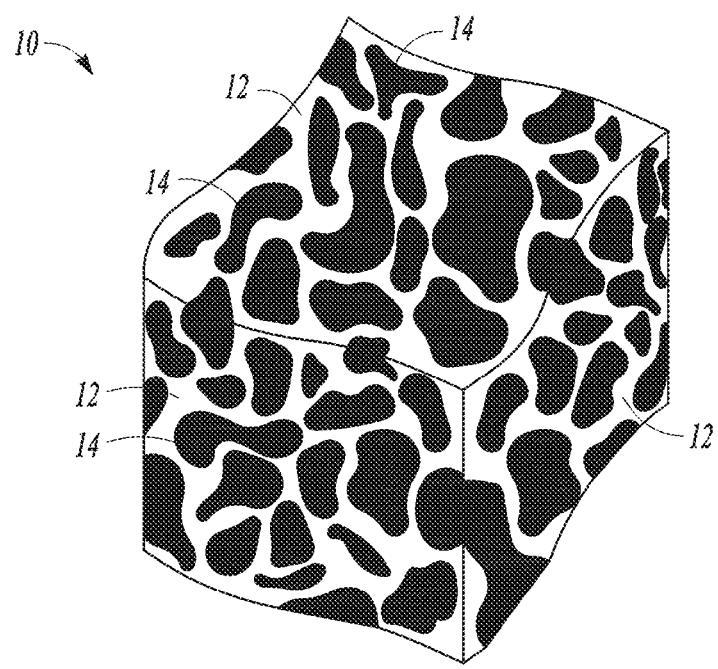
FIG. 1 is a perspective view of an example of a porous metal scaffold.

FIG. 1 illustrates a perspective view of an example porous metal scaffold 10 that can be used to provide support to a patient's tissue, such as bone. The porous metal scaffold 10 can also provide for tissue in-growth, which can facilitate attachment between the patient's tissue and an implant including the porous metal scaffold 10. The porous metal scaffold 10 can include a plurality of ligaments 12 that can define a plurality of open cells 14. The cells 14 can be interconnected by one or more pores. In varying examples, at least about 80%, 90%, 95%, 99%, or even 100% of the cells 14 are interconnected by one or more pores. The pores can help allow or promote in-growth of bone or other tissue cells into and throughout the cells 14. The overall porosity of the porous metal scaffold 10, e.g., the volume percent of open space within the porous metal scaffold 10, can be within a range from about 20% to about 90%, such as within a range from about 20% to about 80%, inclusive, or within a range of from about 50% to about 80%, inclusive.

Figure 2:
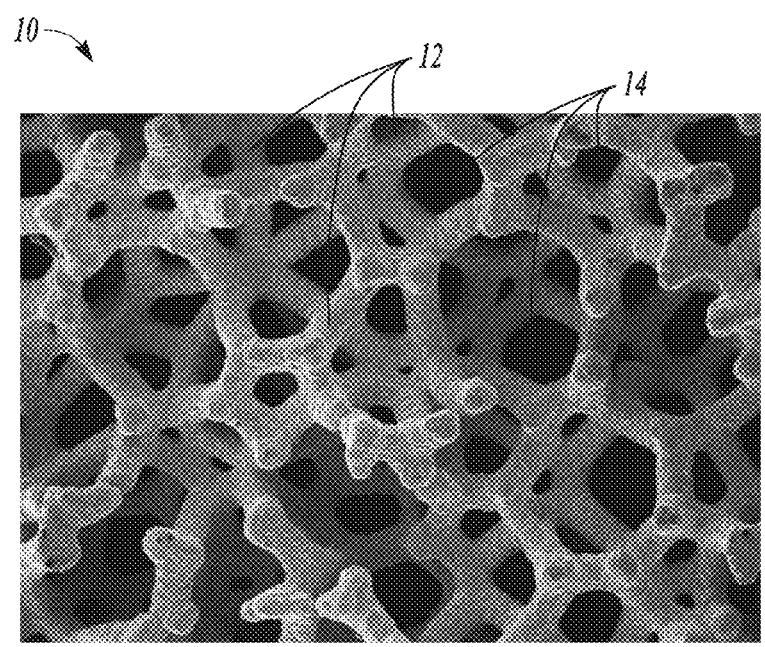
FIG. 2 is an electron micrograph of an example of a porous metal scaffold.

FIG. 2 illustrates a scanning electron micrograph (SEM) of an example of a porous metal scaffold 10 known by the trade name TRABECULAR METAL™, available from Zimmer, Inc., of Warsaw, Ind., USA.

The porous metal scaffold 10 can be made by forming or obtaining a polymeric foam, such as polyurethane foam, with a desired pore structure. The polymeric foam can be engineered to provide one or more of a desired pore size or range of pore sizes, a desired pore shape or pore shapes, a desired aspect ratio or aspect ratios of the pores, or a desired interconnectivity or range of interconnectivities.

The polymeric foam can be converted to form a support scaffold. The conversion process can include chemically treating and pyrolyzing the polymeric foam to form a carbon scaffold. The polymeric foam can be pyrolyzed such that the resulting elemental carbon scaffold has substantially the same geometry as the original polymeric foam (e.g., with pores in substantially the same location with substantially the same pore size, substantially the same pore shape, substantially the same aspect ratio, and substantially the same interconnectivity). In an example, the pyrolyzed polymeric foam can form a reticulated vitreous carbon.

After being formed, the support scaffold can be shaped as desired. The shaping process can include machining, cutting, or otherwise shaping the support scaffold, such as to provide the desired final macroscopice shape of the porous support scaffold.

Figure 3:
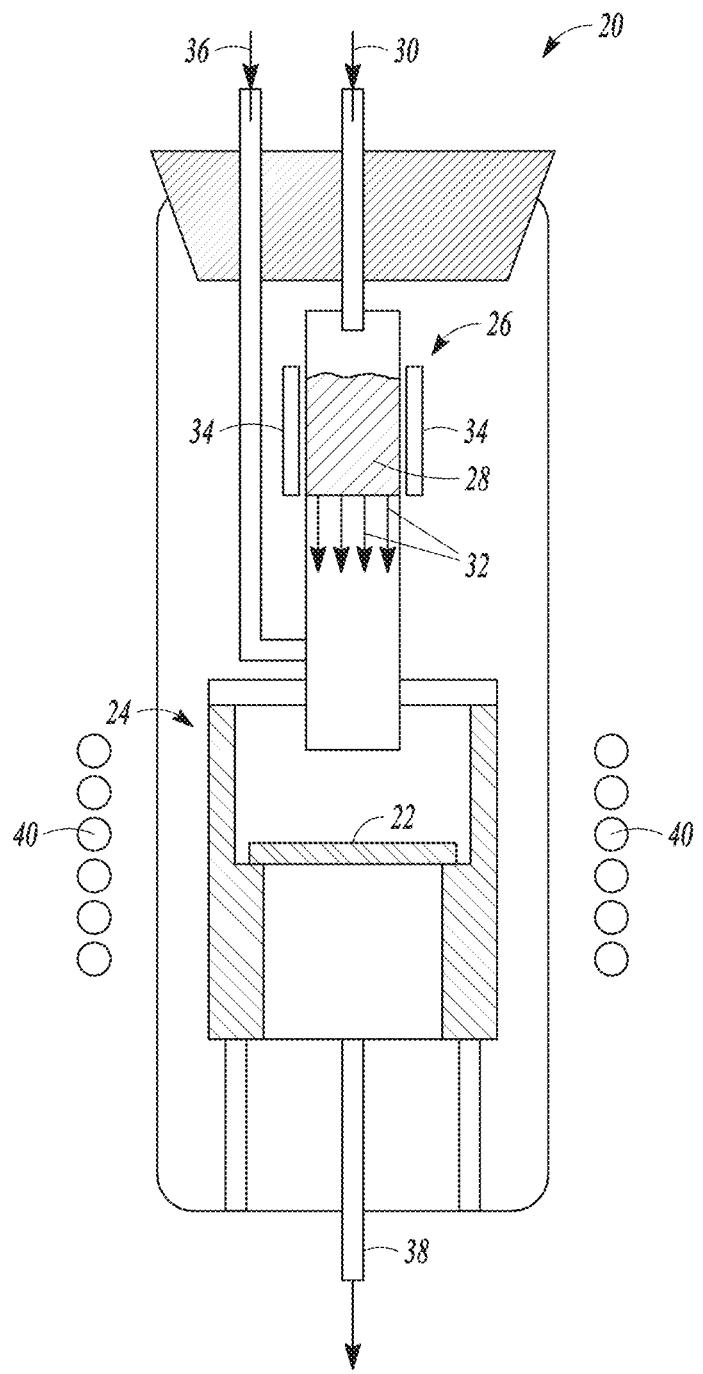
FIG. 3 is a schematic diagram of an example of an apparatus for making a porous metal scaffold

After shaping the support scaffold, a metal can be deposited or otherwise incorporated into the support scaffold, such as via thermal or other chemical vapor deposition (CVD) processes. FIG. 3 illustrates an example of a reactor apparatus 20 configured for thermal CVD of tantalum onto a porous support scaffold 22, such as a reticulated vitreous carbon substrate. The porous support scaffold 22 can be placed in a deposition chamber 24 within the reactor apparatus 20. The reactor apparatus 20 can also include a chlorination chamber 26. Tantalum metal 28 can be placed in the chlorination chamber 26. Chlorine gas ($C_2$) 30 can be injected into the chlorination chamber 26 to react with the tantalum metal 28 to form tantalum pentachloride gas ($TaCl_5$) 32. The tantalum metal 28 and the chlorine gas 30 can be heated with a resistance heater 34 to heat the mixture to a reaction temperature sufficient to form the tantalum pentachloride gas 32.

Hydrogen gas ($H_2$) 36 can also be injected into the reactor apparatus 20. The hydrogen gas 36 and the tantalum pentachloride gas 32 can react with one another in the deposition chamber 24 to deposit tantalum metal onto the porous support scaffold 22 and to form hydrogen chloride (HCl) gas, which can exit the reactor apparatus 20 through an exhaust 38. The deposition chamber 24 can be a furnace, such as a graphite hot wall furnace, that is heated by a heater 40, such as an induction heating coil. The heater 40 can heat the porous support scaffold 22, the tantalum pentachloride 32, and the hydrogen gas 36 to a reaction temperature that is sufficient to deposit the tantalum via thermal CVD onto the porous support scaffold 22 to form a porous metal scaffold 10.

The CVD of tantalum or other metal can form a substantially uniform, thin film of the tantalum or other metal onto the porous support scaffold 22, without affecting its open cell structure. The metal deposition can form a nanotextured structure on the surface of the porous support scaffold 22. The nanotextured surface can help promote attachment of bone or soft tissue to the porous metal scaffold 10. Materials other than tantalum can be additionally or alternatively deposited onto the porous support scaffold 22, such as, but not limited to, niobium, hafnium, tungsten, titanium, an alloy comprising at least one of tantalum, niobium, hafnium, tungsten, or titanium.

After depositing the one or more metal or other materials onto the porous support scaffold 22, the surface of the deposited metals or other materials can be further shaped, such as by machining This can include electric discharge machining, in which an electric arc can be used to machine the surface of the metals or other materials, such as to help ensure that the nanotextured surface or pores of the porous metal scaffold 10 are not compromised or occluded.

When excessive hydrogen atoms are present within the structure of a porous metal scaffold, the hydrogen can cause impaired mechanical properties, including reduced strength or stiffness or increased brittleness. The present systems and methods can reverse or reduce these impaired mechanical properties via out-gassing of the hydrogen from the porous metal scaffold, thereby restoring the mechanical property, such as ductility, mechanical strength, or stiffness, of the porous metal scaffold.

The presence of hydrogen in a porous metal scaffold, such as the porous metal scaffold 10 described above, can occur because of the presence of hydrogen gas used during deposition of tantalum metal or other materials onto the porous support scaffold 22 that forms the porous metal scaffold 10. The present systems and methods described herein can be configured to remove hydrogen that is present in the porous metal scaffold 10, via a combination of one or more of heat, vacuum pressure, and flowing of an inert gas. Heating the porous metal scaffold 10, for example, can cause the scaffold to expand and allow hydrogen atoms or molecules to exit from between metal molecules of the porous metal scaffold 10. The present systems and methods can also induce the hydrogen to diffuse out of or otherwise exit the porous metal scaffold 10.

Figure 4:
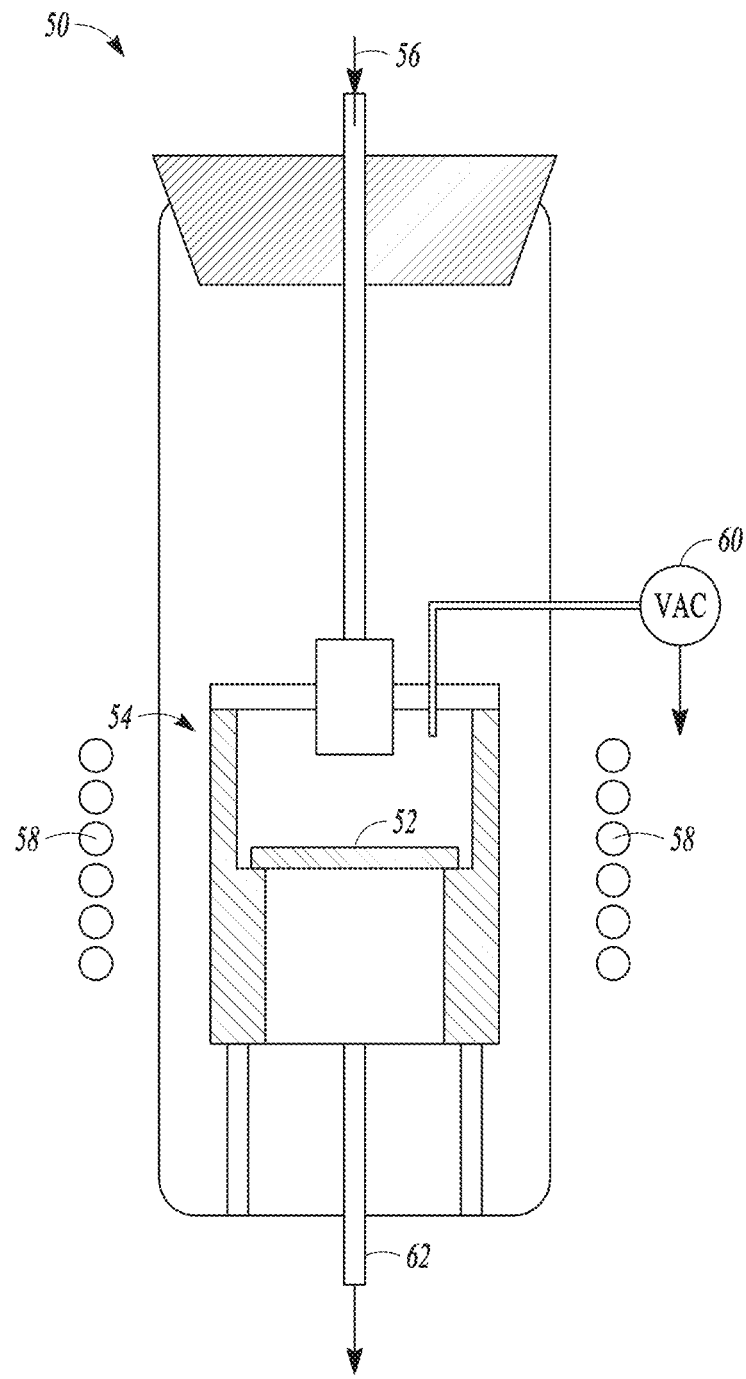
FIG. 4 is a schematic diagram of an example of an apparatus for treating a porous metal scaffold.

FIG. 4 is a schematic diagram of an example of a treating apparatus 50 for treating a porous metal scaffold 52, which can be similar to the porous metal scaffold 10 described above. When a particular porous metal scaffold 52 is determined to have reduced or inadequate ductility, mechanical strength, or stiffness, the weakened porous metal scaffold 52 can be placed in a treating chamber 54 of the treating apparatus 50. An inert gas 56 can be injected into the treating chamber 54 and can flow through or around the weakened porous metal scaffold 52. The term "inert gas," as used herein, can refer to a gas or gas mixture including components that will not react, or that will be substantially unreactive, with the metals or other materials of the porous metal scaffold 52 at conditions within the treating chamber 54. In an example, the inert gas includes only components that will not react or that will be substantially unreactive with the metals or other materials of the porous metal scaffold 52. An example of an inert gas that can be used is argon. Other inert gases can be used, such as other nobel gases including helium, neon, krypton, or xenon.

The treating chamber 54 can be a furnace, such as a graphite hot wall furnace, that is heated by a heater 58, such as an induction heating coil. The heater 58 can heat the porous support scaffold 52 and the inert gas 56 to a temperature sufficient to remove at least a portion of a hydrogen concentration from the porous metal scaffold 52. The temperature of the treating chamber 54 can be selected to provide for thermodynamically-favorable conditions that can lead to hydrogen within the porous metal scaffold 52 being driven out of the scaffold's structure and carried away by the flow of the inert gas 56.

In the case of a porous metal scaffold 52 comprising tantalum metal that is experiencing hydrogen embrittlement, it has been found that a scaffold temperature of at least 1000° C. (about 1830° F.), and in an example at least 1050° C. (1922° F.), can provide for removal of at least a portion of the hydrogen concentration. The temperature of the porous metal scaffold 52 can be controlled, such as by controlling the output of the heater 58, to be as close to 1050° C. (1922° F.) as is practical. In varying examples, the temperature of the porous metal scaffold 52 is controlled to be within ±about 14° C. (about 25° F.) of 1050° C. (1922° F.), such as within ±about 6° C. (about 11° F.) of 1050° C. (1922° F.). In an example, the temperature of the treating chamber 54 can be controlled so that the temperature of the porous metal scaffold 52 is between 1035° C. (1895° F.) and 1065° C. (1949° F.), inclusive, or between 1044° C. (about 1911° F.) and 1056° C. (about 1933° F.), inclusive.

The treating chamber 54 can be subjected to a vacuum through the use of a connected vacuum device 60 (e.g., a vacuum pump), so that while the porous metal scaffold 52 is being treated it can be subjected to a vacuum. The pressure that is provided in the treating chamber 54, along with the temperature within the treating chamber 54, can be sufficient to drive the removal of hydrogen present in the porous metal scaffold 52. The exiting hydrogen can be removed within the inert gas 56. The vacuum device 60 can be configured to provide a pressure of less than 330 pascal (2.5 torr), such as less than about 130 pascal (about 1 torr). In an example, the vacuum device 60 can be configured so that the porous metal scaffold 52 is subjected to a pressure between 100 pascal (0.75 torr) and 330 pascal (2.5 torr), inclusive.

The vacuum device 60 can be configured to subject the porous metal scaffold 52 to vacuum pressure for the entire time or substantially the entire time that the porous metal scaffold 52 is subjected to an elevated temperature sufficient to remove at least a portion of a hydrogen concentration. The vacuum device 60 can be configured to subject the porous metal scaffold 52 to vacuum pressure until the porous metal scaffold 52 has cooled to a temperature that is low enough so that atmospheric hydrogen will not, or is unlikely to, reintegrate into the porous metal scaffold 52. In an example, it has been found that the vacuum device 60 can be configured to subject the porous metal scaffold 52 to the vacuum pressure until the porous metal scaffold 52 has cooled to less than 250° C. (about 480° F.), such as less than about 150° C. (about 300° F.).

The inert gas 56 can be flowed through or around the porous metal scaffold 52 at a flow rate that is sufficient to provide for an inert, e.g., unreactive, environment throughout or substantially through the entire porous metal scaffold 52. The flow rate of the inert gas 56 can also be selected to be sufficient to carry away the portion of the hydrogen concentration being removed from the porous metal scaffold 52. The flow rate of the inert gas 56 can be selected so that the inert gas 56 will flow through all or substantially all of the porous metal scaffold 52, e.g., through all or substantially all of the cells and pores of the porous metal scaffold 52. Hydrogen that diffuses out of or otherwise exits the porous metal scaffold 52 can be captured by the flowing inert gas 56 and carried away from the porous metal scaffold 52, such as through an exhaust 62. In varying examples, it has been found that the flow rate of the inert gas 56 can be at least about 1000 standard cubic centimeters per minute (sccm), such as 1100 sccm, 1200 sccm, at least 1300 sccm, 1400 sccm, 1500 sccm, 2000 sccm, 2500 sccm, 3000 sccm, 3500 sccm, 4000 sccm, or 5000 sccm. The flow rate of the inert gas 56 can be between 1000 sccm and 5000 sccm, inclusive.

The amount of time that the porous metal scaffold 52 is treated within the treating chamber 54 can depend on several factors, including the amount of hydrogen that is believed to be present in the porous metal scaffold 52, the treating conditions (e.g., temperature, pressure, and inert gas flow) within the treating chamber 54, and the geometry of the porous metal scaffold 52. In an example, the treating time, e.g., the time that the porous metal scaffold 52 is treated by heat, subjected to a vacuum, and encountered by a flow of inert gas 56, is at least 45 minutes, at least 60 minutes, at least 75 minutes, or at least about 90 minutes.

The porous metal scaffold 52 can be subjected to all the desired treating conditions (e.g., temperature, vacuum pressure, and inert gas flow rate) for the entirety of the treating time, and then the porous metal scaffold 52 can be subjected to less than all of the desired treating conditions for a subsequent period of time. For example, the porous metal scaffold 52 can be subjected to an elevated temperature of at least 1050° C., a vacuum pressure of less than 330 pascal (2.5 torr), and an inert gas flow rate of at least 1000 sccm for an initial treating time, such as 60 minutes. After the initial treating time is complete, the heater 58 can be turned off and the porous metal scaffold 52 can be allowed to cool while still maintaining one or more of the other treating conditions, such as vacuum pressure or inert gas flow rate, for a subsequent treating time or until a desired condition is met, such as a temperature at or below a threshold.

The treating chamber 54 can be configured to receive a relatively large porous metal scaffold 52, such as a porous metal scaffold 52 that has a volume of at least about 1000 cm$^3$ (about 61 inch$^3$), at least about 2000 cm$^3$ (about 122 inch$^3$), or at least about 2500 cm$^3$ (about 153 inch$^3$). In an example, the treating chamber 54 can be configured to receive a porous metal scaffold 52 having a volume between 1000 cm$^3$ (about 61 inch$^3$) and 5000 cm$^3$ (about 305 inch$^3$), inclusive, or between 2000 cm$^3$ (122 inch$^3$) and 3000 cm$^3$ (183 inch$^3$), inclusive, such as about 2750 cm$^3$ (about 168 inch$^3$). In an example, a porous metal scaffold 52 can include a generally cylindrical body having a diameter of between 10 cm (about 3.9 inch) and 50 cm (about 19.7 inch), inclusive, or between 15 cm (about 5.9 inch) and 40 cm (about 15.7 inch), inclusive, for example about 30 cm (about 12 inch), and a height or depth of between 0.5 cm (about 0.195 inch) and 25 cm (about 9.8 inch), inclusive, or between 1 cm (about 0.39 inch) and 10 cm (about 3.9 inch), inclusive, for example about 3.8 cm (about 1.5 inch).

The treating chamber 54 can have a volume of at least 500 cm$^3$ (about 30.5 inch$^3$), at least 1000 cm$^3$ (about 61 inch$^3$), at least 2500 cm$^3$ (about 153 inch$^3$), at least 5000 cm$^3$ (about 305 inch$^3$), at least 7500 cm$^3$ (about 458 inch$^3$), at least 8000 cm$^3$ (about 488 inch$^3$), at least 10000 cm$^3$ (about 610 inch$^3$), at least 15000 cm$^3$ (about 915 inch$^3$), at least 20000 cm$^3$ (about 1220 inch$^3$), at least 25000 cm$^3$ (about 1526 inch$^3$), or at least 30000 cm$^3$ (about 1861 inch$^3$), for example about 33365 cm$^3$ (about 2036 inch$^3$). In an example, the treating chamber 54 can have a volume of between 9000 cm$^3$ (about 550 inch$^3$) and 35000 cm$^3$ (about 2136 inch$^3$). The shape of the treating chamber 54 can be selected to correspond to a shape of the porous metal scaffold 52, such as a generally cylindrical treating chamber 54 configured to correspond to a generally cylindrical porous metal scaffold 52. In an example, a generally cylindrical treating chamber 54 has a diameter of between 5 cm (about 1.9 inch) and 75 cm (about 30 inch), inclusive, or between 10 cm (about 3.9 inch) and 50 cm (about 19.7 inch), inclusive, for example between 15 cm (about 5.9 inch) and 30 cm (about 11.8 inch), and a height of between 10 cm (about 3.9 inch) and 75 cm (about 30 inch), inclusive, or between 25 cm (about 9.8 inch) and 50 cm (about 19.7 inch), inclusive, for example between 35 cm (about 13.8 inch) and 46 cm (about 18.1 inch).

As can be seen from a comparison of FIGS. 3 and 4, the treating apparatus 50 can be configured similar to the reactor apparatus 20 that is used to deposit a material, such as tantalum metal 28, onto a porous support scaffold 22 to form a porous metal scaffold 10. The same or similar apparatus design can be used for the deposition of a material of the porous metal scaffold 10 and for treatment of a weakened porous metal scaffold 52 for the removal of hydrogen. For example, the reactor apparatus 20 can also be used for the removal of hydrogen, except that rather than feeding chlorine gas 30 and hydrogen gas 36 through the reactor apparatus 20, inert gas 56, such as argon, can be fed through the reactor apparatus 20. Also, the chlorination chamber 26 can be left empty of material, such as the tantalum metal 28, or the chlorination chamber 26 can be configured to be bypassed by the inert gas 56. The heater 40 for heating the deposition chamber 24 and, if desired, the resistance heater 34 for heating the chlorination chamber 26 can be configured so that the porous metal scaffold 52 and the inert gas 56 can reach a temperature that will provide for removal of hydrogen gas from the porous metal scaffold 52.

Figure 5:
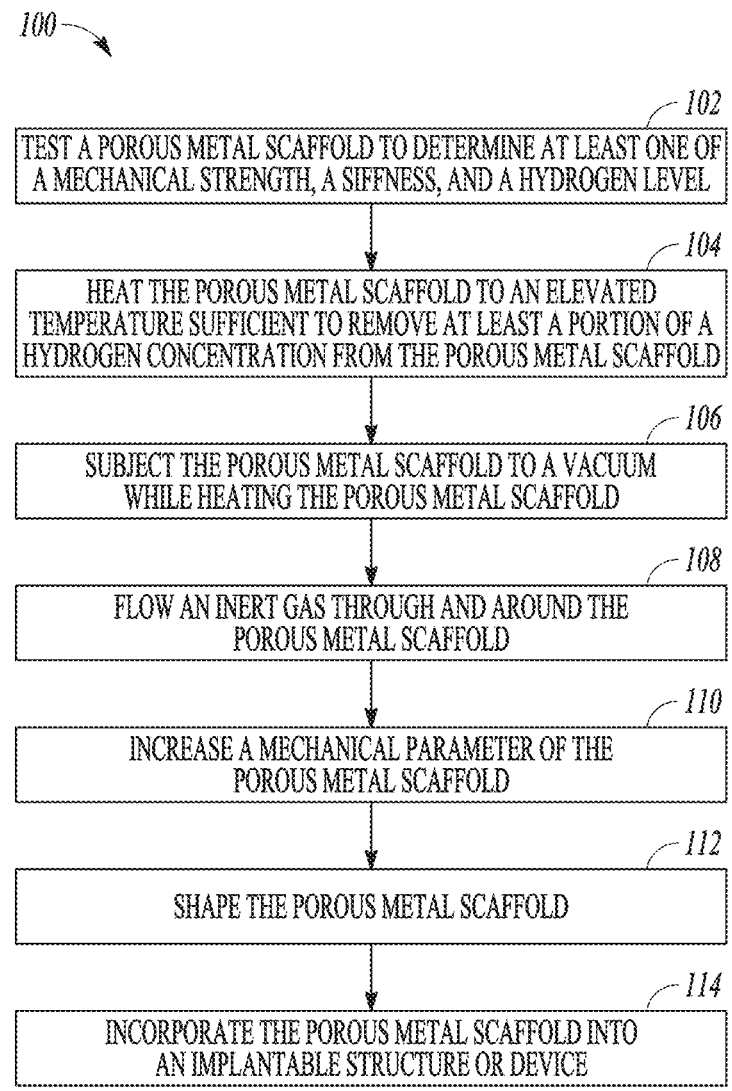
FIG. 5 is a diagram of an example of a method of treating a porous metal scaffold.

FIG. 5 illustrates an example method 100 of treating a porous metal scaffold experiencing hydrogen embrittlement, such as a porous tantalum scaffold, in order to remove at least a portion of a hydrogen concentration from the porous metal scaffold. The method 100 can include, at 102, testing a porous metal scaffold to determine at least one of ductility of the porous metal scaffold, a mechanical strength of the porous metal scaffold, a stiffness of the porous metal scaffold, or a hydrogen level in the porous metal scaffold. If the result of testing indicates an undesirable value of the tested parameter or parameters, then the particular porous metal scaffold may be subjected to treatment to remove hydrogen from the porous metal scaffold. If the result of the testing indicates that the tested parameter or parameters are within an acceptable or adequate range, then the porous metal scaffold can be further processed or prepared for its final application.

The ductility or mechanical strength of the porous metal scaffold can be tested by measuring the compressive strength of the scaffold. A sample of the porous metal scaffold can be subjected to a compressive stress under a particular stress profile until the sample is deformed by a particular predetermined amount or until the sample fails. A stress testing procedure, such as a tensile stress test or a compressive stress test, can include application of a monotonically increasing load that is applied to the sample until a specified displacement of the porous metal scaffold is observed, such as about 0.1 cm (about 0.04 inch). If the value of the ductility or the compressive strength is below a particular strength threshold, the test can indicate that treatment of the porous metal scaffold may be desirable. In an example with a porous tantalum metal scaffold, it has been found that the compressive strength threshold can be selected to be about 24000 psi (about 165.5 megapascal).

Other mechanical properties of the porous metal scaffold can also be tested to determine if treatment of the porous metal scaffold might be desirable. Examples of mechanical properties that can be tested include, but are not limited to, tensile strength, shear modulus, yield strength, maximum strength, or stiffness.

Figure 6A:
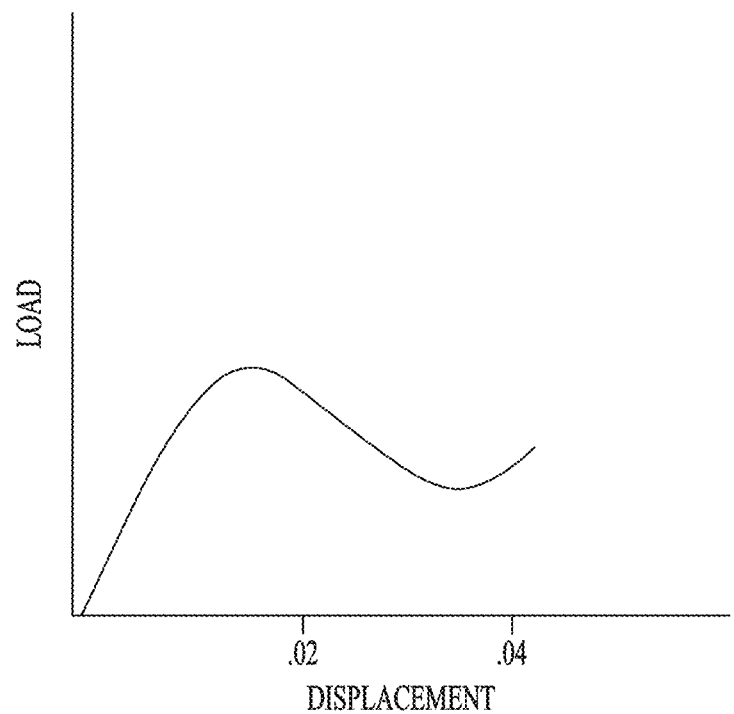
FIG. 6A is a graph illustrating a load-displacement curve of a porous metal scaffold exhibiting ductile behavior.
Figure 6B:
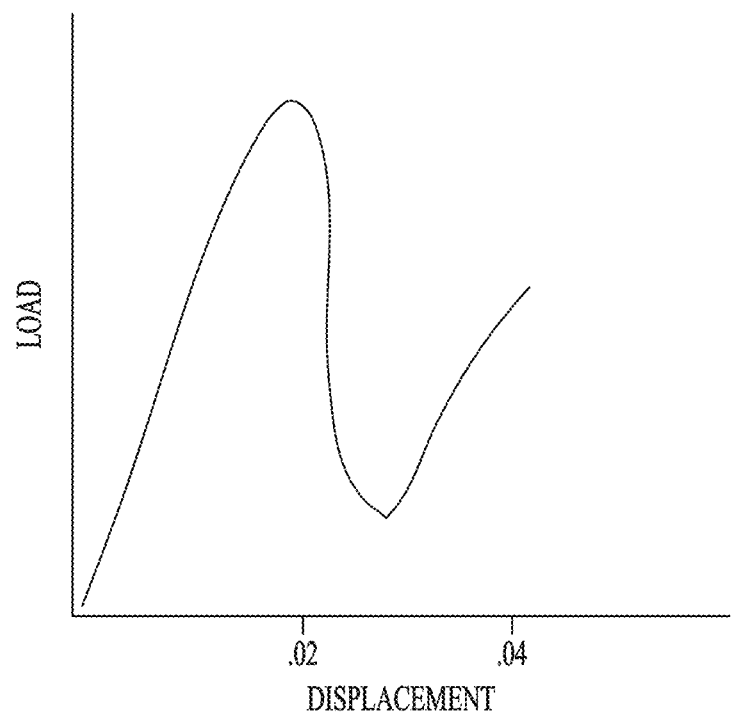
FIG. 6B is a graph illustrating a load-displacement curve of a porous metal scaffold exhibiting brittle behavior.

Another mechanical property that can be tested for is the presence of brittle behavior by the porous metal scaffold. "Brittle behavior," as used herein, can refer to a sudden or steep decrease in load during mechanical testing. Brittle behavior can contrast to ductile behavior. FIG. 6A illustrates a graph of a load-deformation curve, also referred to as a stress-strain curve, of a tantalum porous metal scaffold exhibiting ductile behavior that can be acceptable for orthopedic implant applications. FIG. 6B illustrates a graph of a load-deformation curve of a tantalum porous metal scaffold exhibiting brittle behavior that can be unacceptable for orthopedic implant applications. As can be seen in FIG. 6B, the brittle behavior can be characterized by a sharp drop in load to less than 50% of the peak load. The brittle behavior can also be indicated by the porous metal scaffold fracturing within the first 0.04 inches (about 0.1 cm) of deformation. The test for brittle behavior can be the same as that for compressive strength, but with a recording and inspection of the load-deformation curve.

The hydrogen level of the porous metal scaffold can be tested by chemically analyzing a sample of the scaffold. If the hydrogen level within the porous metal scaffold is higher than a particular predetermined hydrogen threshold, the test can indicate that treatment of the porous metal scaffold may be desirable. In an example of a porous tantalum metal scaffold, it has been found that the hydrogen threshold can be selected to be 500 ppmw, or 0.05 wt %. Lower threshold values can also be used, such as 150 ppmw, or 0.015 wt %, such that any hydrogen level that is greater than 150 ppmw indicates that treatment can be beneficial.

At 104, after testing and determining that a particular porous metal scaffold can benefit from treatment, the scaffold can be heated to an elevated temperature. The elevated temperature can be sufficient to remove at least a portion of a hydrogen concentration from the porous metal scaffold. The temperature of the porous metal scaffold can also be maintained to be within a temperature range that is sufficient to promote removal of hydrogen from the porous metal scaffold. The temperature that the porous metal scaffold is heated to, and maintained at, can be sufficient to promote reaction of the hydrogen out of the porous metal scaffold, such as by reacting two hydrogen atoms to form a hydrogen gas molecule ($H_2$).

In has been found that the reaction mechanism of the hydrogen from the porous metal scaffold can be similar to the reaction mechanism experienced by hydrogen atoms during deposition of tantalum onto a support structure. Specifically, a hydrogen atom can separate from the tantalum and react with another species, e.g., another hydrogen atom in the case of hydrogen removal or a chlorine atom in the case of tantalum deposition. Therefore, the method can include heating a porous tantalum scaffold to a temperature that is similar to a temperature used for the deposition of the tantalum. In an example, the porous metal scaffold can be heated to, and maintained at, a temperature of at least 1000° C. (about 1830° F.), such as at least 1050° C. (1922° F.), to provide for removal of at least a portion of the hydrogen concentration within the porous scaffold.

The temperature of the porous metal scaffold can be controlled to be as close to 1050° C. (1922° F.) as is practical, such as by controlling the temperature of the porous metal scaffold to be within ±about 14° C. (about 25° F.) of 1050° C. (1922° F.) or within ±about 6° C. (about 11° F.) of 1050° C. (1922° F.). In an example, the porous metal scaffold can be controlled to be between 1035° C. (1895° F.) and 1065° C. (1949° F.), inclusive, or between 1044° C. (about 1911° F.) and 1056° C. (about 1933° F.), inclusive.

The temperature of the porous metal scaffold can be maintained for a period of time that is sufficient to remove at least a portion of a hydrogen concentration from the porous metal scaffold. The time period that the porous metal scaffold is subjected to the elevated temperature can be at least 45 minutes, at least 60 minutes, at least 75 minutes, or at least 90 minutes.

At 106, the porous metal scaffold can be subjected to a vacuum while being heated. The porous metal scaffold can be subjected to the vacuum for the time that the porous metal scaffold is maintained at the elevated temperature, e.g., when the temperature of the porous metal scaffold is maintained between 1035° C. and 1065° C., inclusive. The vacuum can also be maintained until the porous metal scaffold cools to a temperature where hydrogen is unlikely to become reincorporated in the porous metal scaffold, such as at a temperature of 250° C. or less or 150° C. or less. The vacuum pressure that the porous metal scaffold is subjected to can be 330 pascal (2.5 torr) or less, such as 130 pascal (about 1 torr) or less. In an example, the porous metal scaffold can be subjected to a pressure between 100 pascal (0.75 torr) and 330 pascal (2.5 torr), inclusive.

At 108, an inert gas, such as argon, can be flowed through or around the porous metal scaffold while the scaffold is heated. The flow of the inert gas can provide for an environment in and around the porous metal scaffold that is unlikely to result in reaction of removed hydrogen being integrated back into the scaffold. The flow of the inert gas can also act as a carrier to carry removed hydrogen away from the porous metal scaffold. The flow rate of the inert gas can between 1000 sccm and 5000 sccm, inclusive.

At 110, a mechanical parameter of the porous metal scaffold can be increased after heating the porous metal scaffold, subjecting the porous metal scaffold to a vacuum, and flowing the inert gas through or around the porous metal scaffold compared to a value of the mechanical parameter before the heating, vacuum, and flowing processes. The level of hydrogen in the porous metal scaffold can also be reduced. In an example, the hydrogen level, in ppmw, can be reduced by between 50% and 90% inclusive, or between 60% and 85%.

After treating the porous metal scaffold, such as at 104, 106, and 108, the scaffold can have a mechanical strength that is at least 24,000 psi. After treating the porous metal scaffold, the brittle behavior illustrated in FIG. 6B can be eliminated and the hydrogen level within scaffold can be less than 150 ppmw.

At 112, the treated porous metal scaffold can be shaped into a form that is configured to be implanted into a patient. By way of example, the treated porous metal scaffold can be shaped into a spinal implant, a femoral support implant, or as an attachment structure for an implant to promote tissue ingrowth and enhance tissue-to-implant attachment. The treated porous metal scaffold can be shaped to change a microscopic or macroscopic shape of the scaffold. Shaping of the porous metal scaffold can include, but is not limited to, machining, cutting, grinding, trimming, or any other shaping technique.

At 114, the treated porous metal scaffold can be incorporated into an implantable structure or device, such as an implantable orthopedic device. Examples of implants where a treated porous metal scaffold can be incorporated include, but are not limited to, a prosthetic shoulder implant, a prosthetic arm implant, a prosthetic elbow implant, a prosthetic finger implant, a prosthetic spine implant, a prosthetic hip implant, a prosthetic leg implant, a prosthetic knee implant, a prosthetic ankle implant, a prosthetic toe implant, a prosthetic bone support implant, a prosthetic spine implant, or a prosthetic trauma implant.

To better illustrate the present systems and methods for treating a porous metal scaffold to reduce effects of hydrogen embrittlement, a non-limiting list of examples is provide here:

In Example 1, a method comprises heating a porous metal scaffold, including maintaining a temperature of the porous metal scaffold between 1035° C. and 1065° C., inclusive, for a period of time sufficient to remove at least a portion of a hydrogen concentration from the porous metal scaffold, subjecting the porous metal scaffold to a vacuum while heating it; flowing an inert gas through or around the porous metal scaffold while heating it; and increasing a mechanical property of the porous metal scaffold.

In Example 2, the method of Example 1 is optionally configured such that flowing the inert gas includes flowing the inert gas through or around the porous metal scaffold when a temperature of the porous metal scaffold is greater than or equal to a temperature of 250° C.

In Example 3, the method of either of Examples 1 or 2 is optionally configured such that subjecting the porous metal scaffold to the vacuum includes subjecting the porous metal scaffold to a pressure between 100 pascal (0.75 torr) and 330 pascal (2.5 torr), inclusive.

In Example 4, the method of Example 4 is optionally configured such that subjecting the porous metal scaffold to the vacuum includes subjecting the porous metal scaffold to a pressure between 100 pascal (0.75 torr) and 330 pascal (2.5 torr), inclusive, when a temperature of the porous metal scaffold is greater than or equal to a temperature of 250° C.

In Example 5, the method of any one of Examples 1-4 is optionally configured such that flowing the inert gas includes flowing the inert gas through or around the porous metal scaffold while maintaining the temperature of between 1036° C. and 1064° C., inclusive.

In Example 6, the method of any one of Examples 1-5 is optionally configured such that subjecting the porous metal scaffold to the vacuum includes subjecting the porous metal scaffold to the vacuum while maintaining the temperature of between 1036° C. and 1064° C., inclusive.

In Example 7, the method of any one of Examples 1-6 is optionally configured such that flowing the inert gas includes flowing the inert gas at a flow rate sufficient to carry away the portion of the hydrogen concentration being removed from the porous metal scaffold.

In Example 8, the method of Example 7 is optionally configured such that flowing the inert gas at the flow rate sufficient to carry away the portion of the hydrogen concentration includes flowing the inert gas at a rate of at least about 1000 standard cubic centimeters per minute.

In Example 9, the method of any one of Examples 1-8 is optionally configured such that flowing the inert gas includes flowing argon through or around the porous metal scaffold.

In Example 10, the method of any one of Example 1-9 is optionally configured such that maintaining the temperature of the porous metal scaffold includes maintaining the temperature of the porous metal scaffold between 1044° C. and 1056° C., inclusive.

In Example 11, the method of any one of Examples 1-10 is optionally configured such that maintaining the temperature of the porous metal scaffold includes maintaining the temperature of the porous metal scaffold for at least 60 minutes.

In Example 12, the method of any one of Examples 1-11 optionally further comprises placing the porous metal scaffold in a reaction chamber having a volume of at least 500 cm$^3$.

In Example 13, the method of any one of Examples 1-12 optionally further comprises the mechanical property including at least one of ductility and mechanical strength.

In Example 14, a system comprises a reaction chamber for receiving a porous metal scaffold, a heater configured to heat the reaction chamber and the porous metal scaffold and to maintain a temperature of the porous metal scaffold between 1035° C. and 1065° C., inclusive, for a period of time sufficient to remove at least a portion of a hydrogen concentration from the porous metal scaffold, a gas feed for feeding an inert gas, the gas feed being configured to flow the inert gas through or around the porous metal scaffold while the heater heats the reaction chamber and the porous metal scaffold, and a vacuum apparatus configured to subject the porous metal scaffold to a vacuum while the heater heats the porous metal scaffold.

In Example 15, the system of Example 14 is optionally configured such that the gas feed is configured to flow the inert gas through or around the porous metal scaffold when a temperature of the porous metal scaffold is greater than or equal to a temperature of 250° C.

In Example 16, the system of either of Examples 14 or 15 is optionally configured such that the vacuum device is configured to subject the porous metal scaffold to a pressure between 100 pascal (0.75 torr) and 330 pascal (2.5 torr), inclusive.

In Example 17, the system of any one of Examples 14-16 is optionally configured such that the gas feed is configured to flow the inert gas at a flow rate sufficient to carry away the portion of the hydrogen concentration being removed from the porous metal scaffold.

In Example 18, the system of any one of Examples 14-17 is optionally configured such that the gas feed is configured to flow the inert gas at the flow rate of at least about 1000 standard cubic centimeters per minute.

In Example 19, the system of any one of Examples 14-18 is optionally configured such that the reaction chamber has a volume of at least 500 $cm^3$.

In Example 20, a method comprises heating a porous metal scaffold for a period of time sufficient to remove at least a portion of a hydrogen concentration from the porous metal scaffold, subjecting the porous metal scaffold to a vacuum while heating the porous metal scaffold, flowing an inert gas through or around the porous metal scaffold while heating the porous metal scaffold, and enhancing a mechanical property of the porous metal scaffold.

In Example 21, the method of Example 20 is optionally configured such that heating the porous metal scaffold includes maintaining a temperature of the porous metal scaffold above 1000° C. for at least 60 minutes.

In Example 22, the method of either of Examples 20 or 21 is optionally configured such that flowing the inert gas includes flowing argon through or around the porous metal scaffold.

In Example 23, the method of any one of Examples 20-22 optionally further comprises the mechanical property including at least one of ductility and mechanical strength.

In Example 24, the system or method of any one or any combination of Examples 1-23 is optionally configured such that all elements or options recited are available to use or select from.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented, at least in part. Some examples can include a computer-readable medium or machine-readable medium encoded with instructions operable to configure an electronic device to perform methods or method steps as described in the above examples. An implementation of such methods or method steps can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. A method comprising:
heating a porous metal scaffold, said heating including maintaining a temperature of the porous metal scaffold between 1035° C. and 1065° C., inclusive, for a period of time sufficient to remove at least a portion of a hydrogen concentration from the porous metal scaffold, the porous metal scaffold comprising an underlying porous support scaffold with a metal coating chemical vapor deposited onto and within the underlying porous support scaffold;
subjecting the porous metal scaffold to a vacuum while heating the porous metal scaffold;

flowing an inert gas through or around the porous metal scaffold while heating the porous metal scaffold; and
increasing a mechanical property of the porous metal scaffold.

2. The method of claim 1, wherein flowing the inert gas includes flowing the inert gas through or around the porous metal scaffold when a temperature of the porous metal scaffold is greater than or equal to a temperature of 250° C.

3. The method of claim 1, wherein subjecting the porous metal scaffold to the vacuum includes subjecting the porous metal scaffold to a pressure between 100 pascal (0.75 torr) and 330 pascal (2.5 torr), inclusive.

4. The method of claim 3, wherein subjecting the porous metal scaffold to the vacuum includes subjecting the porous metal scaffold to a pressure between 100 pascal (0.75 torr) and 330 pascal (2.5 torr), inclusive, when a temperature of the porous metal scaffold is greater than or equal to a temperature of 250° C.

5. The method of claim 1, wherein flowing the inert gas includes flowing the inert gas through or around the porous metal scaffold while maintaining the temperature of between 1036° C. and 1064° C., inclusive.

6. The method of claim 1, wherein subjecting the porous metal scaffold to the vacuum includes subjecting the porous metal scaffold to the vacuum while maintaining the temperature of between 1036° C. and 1064° C., inclusive.

7. The method of claim 1, wherein flowing the inert gas includes flowing the inert gas at a flow rate sufficient to maintain an inert atmosphere within the porous metal scaffold.

8. The method of claim 7, wherein flowing the inert gas at the flow rate sufficient to maintain the inert atmosphere within the porous metal scaffold includes flowing the inert gas at a rate of at least about 1000 standard cubic centimeters per minute.

9. The method of claim 1, wherein maintaining the temperature of the porous metal scaffold includes maintaining the temperature of the porous metal scaffold between 1044° C. and 1056° C., inclusive.

10. The method of claim 1, wherein maintaining the temperature of the porous metal scaffold includes maintaining the temperature of the porous metal scaffold for at least 60 minutes.

11. The method of claim 1, wherein the mechanical property comprises at least one of ductility and mechanical strength.

12. The method of claim 1 further comprising testing said porous metal scaffold prior to said heating to determine a hydrogen level of said porous metal scaffold.

13. A method comprising:
heating a porous metal scaffold for a period of time sufficient to remove at least a portion of a hydrogen concentration from the porous metal scaffold, the porous metal scaffold comprising an underlying porous support scaffold with a metal coating on and within the underlying porous support scaffold:
subjecting the porous metal scaffold to a vacuum while heating the porous metal scaffold;
flowing an inert gas through or around the porous metal scaffold while heating the porous metal scaffold; and
enhancing a mechanical property of the porous metal scaffold.

14. The method of claim 13, wherein heating the porous metal scaffold includes maintaining a temperature of the porous metal scaffold above 1000° C. for at least 60 minutes.

15. The method of claim 13, wherein subjecting the porous metal scaffold to the vacuum includes subjecting the porous metal scaffold to a pressure between 100 pascal (0.75 torr) and 330 pascal (2.5 torr), inclusive, when a temperature of the porous metal scaffold is greater than or equal to a temperature of 250° C.

16. The method of claim 13, wherein said enhancing the mechanical property comprises increasing at least one of ductility and mechanical strength.

17. The method of claim 16, wherein said heating occurs in a chamber, and wherein the metal coating is a chemical vapor deposited metal coating applied in said chamber prior to said heating.

18. The method of claim 13, wherein the metal coating is a chemical vapor deposited metal coating.

19. The method of claim 18, wherein said heating occurs in a chamber, and wherein the chemical vapor deposited metal coating was applied in said chamber prior to said heating.

20. The method of claim 13, wherein the underlying porous support scaffold is a porous reticulated vitreous carbon substrate.

21. The method of claim 13 further comprising testing said porous metal scaffold prior to said heating to determine a hydrogen level of said porous metal scaffold.

* * * * *